United States Patent
Middlebrooks et al.

(10) Patent No.: US 10,265,040 B2
(45) Date of Patent: Apr. 23, 2019

(54) METHOD AND APPARATUS FOR ADAPTIVE COMPUTER-AIDED DIAGNOSIS

(71) Applicants: Scott Anderson Middlebrooks, Beaverton, OR (US); Henricus Wilhelm van der Heijden, Oud-Turnhout (BE)

(72) Inventors: Scott Anderson Middlebrooks, Beaverton, OR (US); Henricus Wilhelm van der Heijden, Oud-Turnhout (BE)

( * ) Notice: Subject to any disclaimer, the term of this patent is extended or adjusted under 35 U.S.C. 154(b) by 311 days.

(21) Appl. No.: 14/797,756

(22) Filed: Jul. 13, 2015

(65) Prior Publication Data
US 2017/0018075 A1    Jan. 19, 2017

(51) Int. Cl.
| | |
|---|---|
| *A61B 6/00* | (2006.01) |
| *G06N 99/00* | (2019.01) |
| *G06N 5/04* | (2006.01) |
| *G06K 9/62* | (2006.01) |
| *A61B 6/03* | (2006.01) |

(52) U.S. Cl.
CPC ............ *A61B 6/502* (2013.01); *G06K 9/6263* (2013.01); *G06K 9/6292* (2013.01); *G06N 5/045* (2013.01); *G06N 99/005* (2013.01); *A61B 6/032* (2013.01); *A61B 6/5217* (2013.01)

(58) Field of Classification Search
CPC ....... A61B 6/502; A61B 6/032; A61B 6/5217; G06K 9/6263; G06K 9/6292; G06K 2209/05; G06K 9/6254; G06N 5/045; G06N 99/005; G06N 6/032; G06N 3/0427; G06T 7/0012; G06T 7/0014; G06T 5/20; G06T 2207/20081; G06T 2207/30196; G06T 7/246; G16H 50/20
See application file for complete search history.

(56) References Cited

U.S. PATENT DOCUMENTS

| | | | | | |
|---|---|---|---|---|---|
| 6,128,608 | A  * | 10/2000 | Barnhill | ............... | G06K 9/6256 706/12 |
| 6,882,990 | B1 * | 4/2005 | Barnhill | ............... | G06K 9/6228 706/16 |
| 6,996,549 | B2 * | 2/2006 | Zhang | .................... | G06K 9/623 706/12 |
| 7,298,877 | B1 * | 11/2007 | Collins | .................. | G01N 23/04 378/1 |
| 7,828,732 | B2 * | 11/2010 | Wang | ..................... | A61B 6/463 600/437 |
| 8,296,247 | B2 * | 10/2012 | Zhang | .................. | G06F 19/345 706/10 |
| 2017/0018076 | A1 * | 1/2017 | Middlebrooks | ...... | G06K 9/6267 |

* cited by examiner

*Primary Examiner* — Manav Seth

(57) ABSTRACT

The invention provides a method and apparatus for classifying a region of interest in imaging data, the method comprising:

calculating a feature vector for at least one region of interest in the imaging data;

projecting the feature vector for the at least one region of interest in the imaging data using a plurality of decision functions to generate a corresponding plurality of classifications;

calculating an ensemble classification based on the plurality of classifications.

receiving from the user feedback information concerning the ensemble classification;

forming an additional classified feature vector from the feature vector and the feedback information; and updating at least one of the plurality of decision functions using the additional classified feature vector.

10 Claims, 16 Drawing Sheets

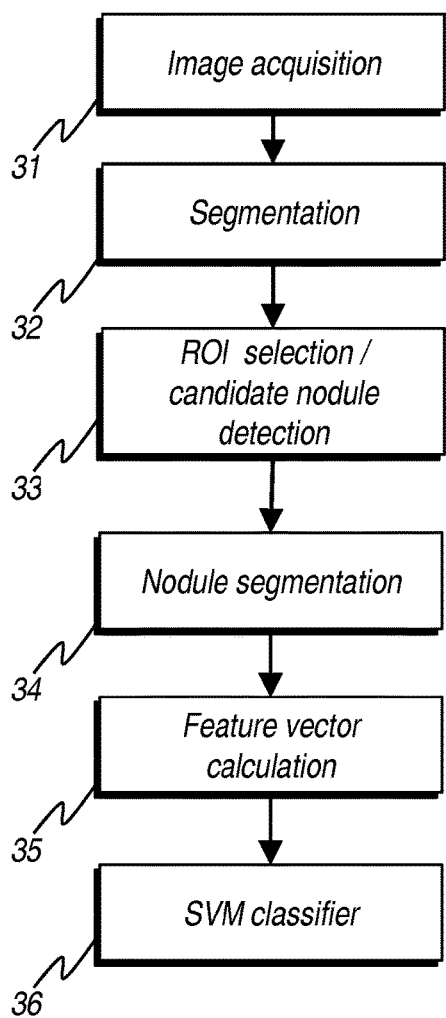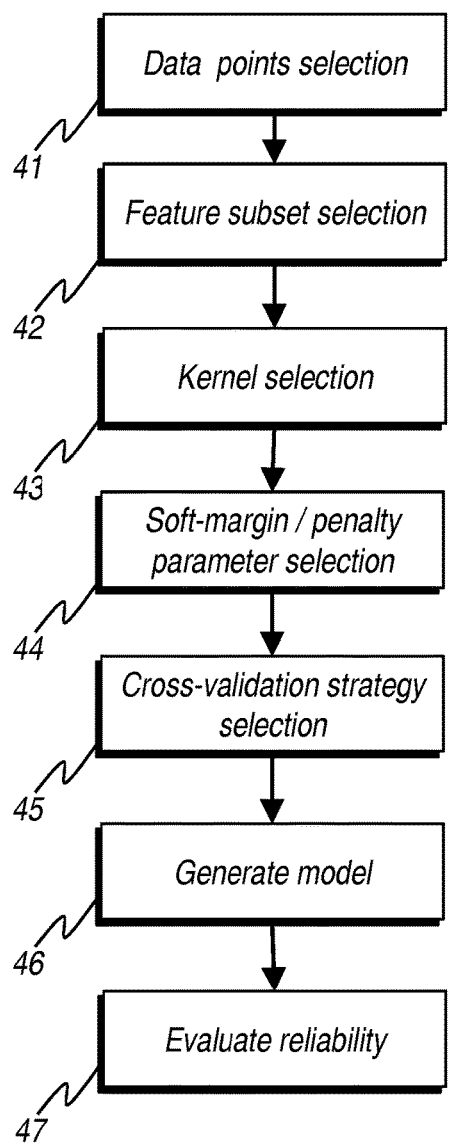

METHOD AND APPARATUS FOR ADAPTIVE COMPUTER-AIDED DIAGNOSIS

FIELD OF THE DISCLOSURE

The disclosure relates to computer-aided diagnosis (CAD). The disclosure also relates to a method and a platform or system for using machine learning algorithms for CAD.

BACKGROUND OF THE DISCLOSURE

Advances in computed tomography (CT) allow early detection of cancer, in particular lung cancer which is one of the most common cancers. As a result, there is increased focus on using regular low-dose CT screenings to ensure early detection of the disease with improved chances of success of the following treatment. This increased focus leads to an increased workload for professionals such as radiologists who have to analyze the CT screenings.

To cope with the increased workload, computer-aided detection (CADe) and computer-aided diagnosis (CADx) systems are being developed. Hereafter both types of systems will be referred to as CAD systems. CAD systems can detect lesions (e.g. nodules) and subsequently classify them as malignant or benign. A classification need not be binary, it can also include a stage of the cancer. Usually, a classification is accompanied with a confidence value as calculated by the CAD system.

CAD systems typically follow a number of general steps. First, the input imaging data is segmented, for example to distinguish lung tissue from the background signal. Then, regions of interest are identified, for example all lung tissue with nodule-like forms in them. For each region of interest a number of input values is calculated, the so-called feature vector. This feature vector is used as input in a decision function, which projects the feature vector to a classification.

Hereafter the term "model" will be used to indicate a computational framework for performing one or more of a segmentation and a classification of imaging data. The segmentation, identification of regions of interest, and/or the classification may involve the use of a machine learning (ML) algorithm. The model comprises at least one decision function, which may be based on a machine learning algorithm, which projects the input to an output. For example, a decision function may project a feature vector to a classification outcome.

A problem with CAD systems based on a ML algorithm is that the system can only function well if sufficient data is available for training. In many cases, academics working on such systems lack sufficient training data. This hampers deployment and acceptance of CAD systems.

SUMMARY OF THE DISCLOSURE

It is an object of this disclosure to provide a method and apparatus for classifying a region of interest in imaging data which addresses the above drawbacks.

The disclosure provides a method for classifying a region of interest in imaging data, the method comprising:
calculating a feature vector for at least one region of interest in the imaging data;
projecting the feature vector for the at least one region of interest in the imaging data using a plurality of decision functions to generate a corresponding plurality of classifications;
calculating an ensemble classification based on the plurality of classifications.

In an embodiment, the method further comprises:
receiving from the user feedback information concerning the ensemble classification;
forming an additional classified feature vector from the feature vector and the feedback information; and
updating at least one of the plurality of decision functions using the additional classified feature vector.

The disclosure provides another method for classifying a region of interest in imaging data, the method comprising:
calculating a feature vector for at least one region of interest in the imaging data;
projecting the feature vector for the at least one region of interest in the imaging data using a first decision function to a classification;
receiving from the user feedback information concerning the classification;
forming an additional classified feature vector from the feature vector and the feedback information; and
updating the first decision function using the additional classified feature vector.

In an embodiment, the method further comprises:
projecting the feature vector for the at least one region of interest in the imaging data using a second decision function to a second classification;
generating an ensemble classification based on at least the first and the second classification.

Further examples are disclosed in the attached claims and described in reference to the figures below.

The disclosure thus relates to an adaptive form of CAD which is able to take advantage of new data becoming available. By aggregating (training) data, models can be improved. By recursively updating the decision function of one or more existing models, the gradual accumulation of data does not require re-training of the existing models using the entire data set, saving time and computation resources.

By calculating an ensemble classification using a plurality of classifications from different models (preferably of the same model type) the models (and therefore by extension the training data on which the models are based) can be aggregated as well.

There are thus two ways in which a gradually increase of available data improves the quality of classifications: by calculating an ensemble classification from an increasing plurality of separate model classifications and by updating decision functions of one or more models as new data becomes available. A combination of both ways can also be used.

The disclosure further provides a computation platform comprising a computation device, configured to implement the above described methods. The disclosure further provides a system of a computation platform and a user terminal, configured to implement the above described methods. The disclosure further provides a non-transitory computer readable medium comprising computer instructions for implementing the methods according the disclosure.

BRIEF DESCRIPTION OF THE FIGURES

Embodiments of the present disclosure will be described hereinafter, by way of example only, with reference to the accompanying drawings which are schematic in nature and therefore not necessarily drawn to scale. Furthermore, like reference signs in the drawings relate to like elements.

FIG. 3 schematically shows a flow chart for a model calculation according to embodiments of the disclosed subject matter.

FIG. 4 schematically shows a flow chart for specifying details of a model calculation according to embodiments of the disclosed subject matter.

DETAILED DESCRIPTION

In the detailed description, captions are merely used to organize the information in a fashion to facilitate reading. These captions are not to be understood as indicating separations between distinct embodiments or distinct aspects of the disclosure.

Computation Platform

Figure 1:
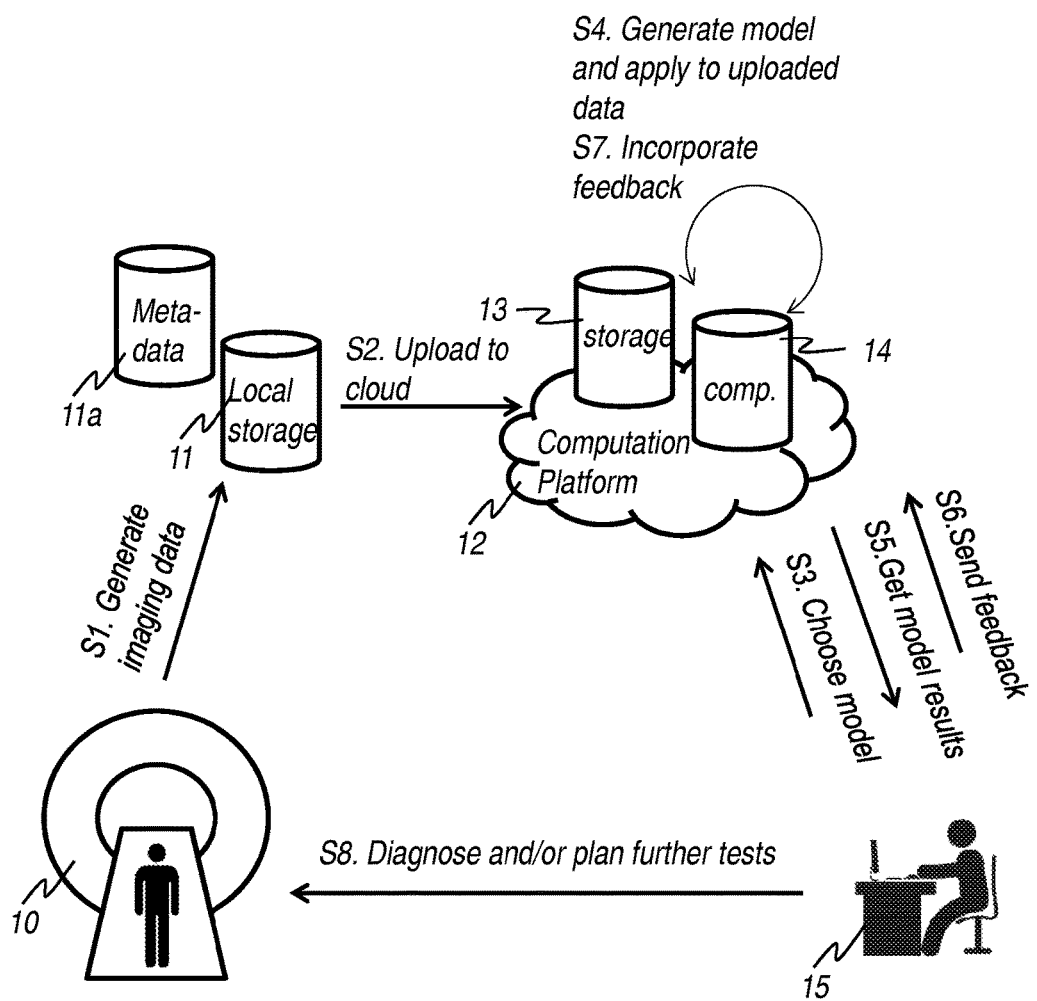
FIG. 1 schematically shows an overview of a workflow according to embodiments of the disclosed subject matter.

FIG. 1 schematically shows an overview of a workflow according to embodiments of the disclosed subject matter. A patient is scanned in scanning device 10. The scanning device 10 can be any type of device for generating diagnostic image data, for example an X-Ray device, a Magnetic Resonance Imaging (MRI) scanner, or any general Computed Tomography (CT) device. Of particular interest are low-dose X-Ray devices for regular and routine scans. The various types of scans can be further characterized by the use of a contrast agent, if any.

In the following, the example of a CT device, in particular a CT device for low dose screenings, will be used. However, this is only exemplary. Aspects of the disclosure can be applied to any instantiation of imaging modality, provided that it is capable of providing imaging data. A distinct type of scan (X-Ray CT, low-dose X-Ray CT, CT with contrast agent X) can be defined as a modality.

The images generated by the CT device 10 (hereafter: imaging data) are sent to a storage 11 (step S1). The storage 11 can be a local storage, for example close to or part of the CT device 10. It can also be part of the IT infrastructure of the institute that hosts the CT device 10. The storage 11 is convenient but not essential. The data could also be sent directly from the CT device 10 to computation platform 12.

All or parts of the imaging data is then sent to the computation platform 12 in step S2. In general it is most useful to send all acquired data, so that the computer models of platform 12 can use all available information. However, partial data may be sent to save bandwidth, to remove redundant data, or because of limitations on what is allowed to be sent (e.g. because of patient privacy considerations). The data sent to the computation platform 12 may be provided with metadata from scanner 10, storage 11, or further database 11a. Metadata can include additional data related to the imaging data. For example statistical data of the patient (gender, age, medical history) or data concerning the equipment used (type and brand of equipment, scanning settings, etc).

Computation platform 12 comprises one or more storage devices 13 and one or more computation devices 14, along with the necessary network infrastructure to interconnect the devices 13, 14 and to connect them with the outside world, preferably via the Internet. It should be noted that the term "computation platform" is used to indicate a convenient implementation means (e.g. via available cloud computing resources). However, embodiments of the disclosure may use a "private platform", i.e. storage and computing devices on a restricted network, for example the local network of an institution or hospital. The term "computation platform" as used in this application does not preclude embodiments of such private implementations, nor does it exclude embodiments of centralized or distributed (cloud) computing platforms.

The imaging data is stored in the storage 13. The central computing devices 14 can process the imaging data to generate feature data as input for the models. The computing devices 14 can segment imaging data. The computing devices 14 can also use the models to classify the (segmented) imaging data. More functionality of the computing devices 14 will be described in reference to the other figures.

A work station 15 for use by a professional, for example a radiologist, is connected to the computation platform 12. Hereafter, the terms "professional" and "user" will be used interchangeably. The work station 15 is configured to receive data and model calculations from the computation platform, and to send instructions and feedback to the computation platform 12. The work station 15 can visualize received raw data and model results.

In step S3, the professional selects a basal model (or in general: specifies model parameters) for use in a calculation. More exemplary details concerning basal models are provided in reference to FIG. 9. Based on the entered model parameters, in step S4 the platform 12 generates the model (if needed—the model may be already cached), performs the needed calculations for training the model (if needed—training data for the model may already be available in the computation platform 12), and applies the model to the imaging data that was received in step S2. In general, the computation platform will use stored results for calculations that have been performed earlier (i.e. calculated image features, model training data) and only perform the calculations it has not done before. This way, the professional accessing the computation platform 12 using the work station 15 can have a fast response to his or her instructions.

The result of the model calculations, for example a segmentation of the imaging data and corresponding classification, is sent to the professional in step S5. The received data is visualized on the work station 15. The professional will examine the results and prepare feedback in step S6. Feedback may for example be that, in the professional's opinion, the presented classification is correct or incorrect. Other types of feedback are also available in exemplary embodiments, for example: the professional can confirm or correct the basic classification (e.g. malignant or benign) and also add further information, for example a stage of the cancer in case of a malign classification. In this manner, the feedback information can be used to enrich the classified feature vectors so that at a later stage more sophisticated models can be trained.

The feedback from step S6 is sent to the computation platform 12. In step S7, the computation platform 12 incorporates the feedback in its own data. For example, if the feedback is of the correct/incorrect or malignant/benign type, the model results and the feedback can be added as ground truths for further training. Along with the feedback, the source of the feedback may also be stored. That makes it possible to train future models using only feedback from selected sources. For example, the professional can request models that are only trained using his own data or data from close colleagues (e.g. "trusted data"). Instead or in addition to this, the feedback can be used incrementally adjust the decisions functions of the model. The feedback can be used only in one or more selected decision functions, again to insure that models are trained using data from known and trusted sources.

Figure 2:
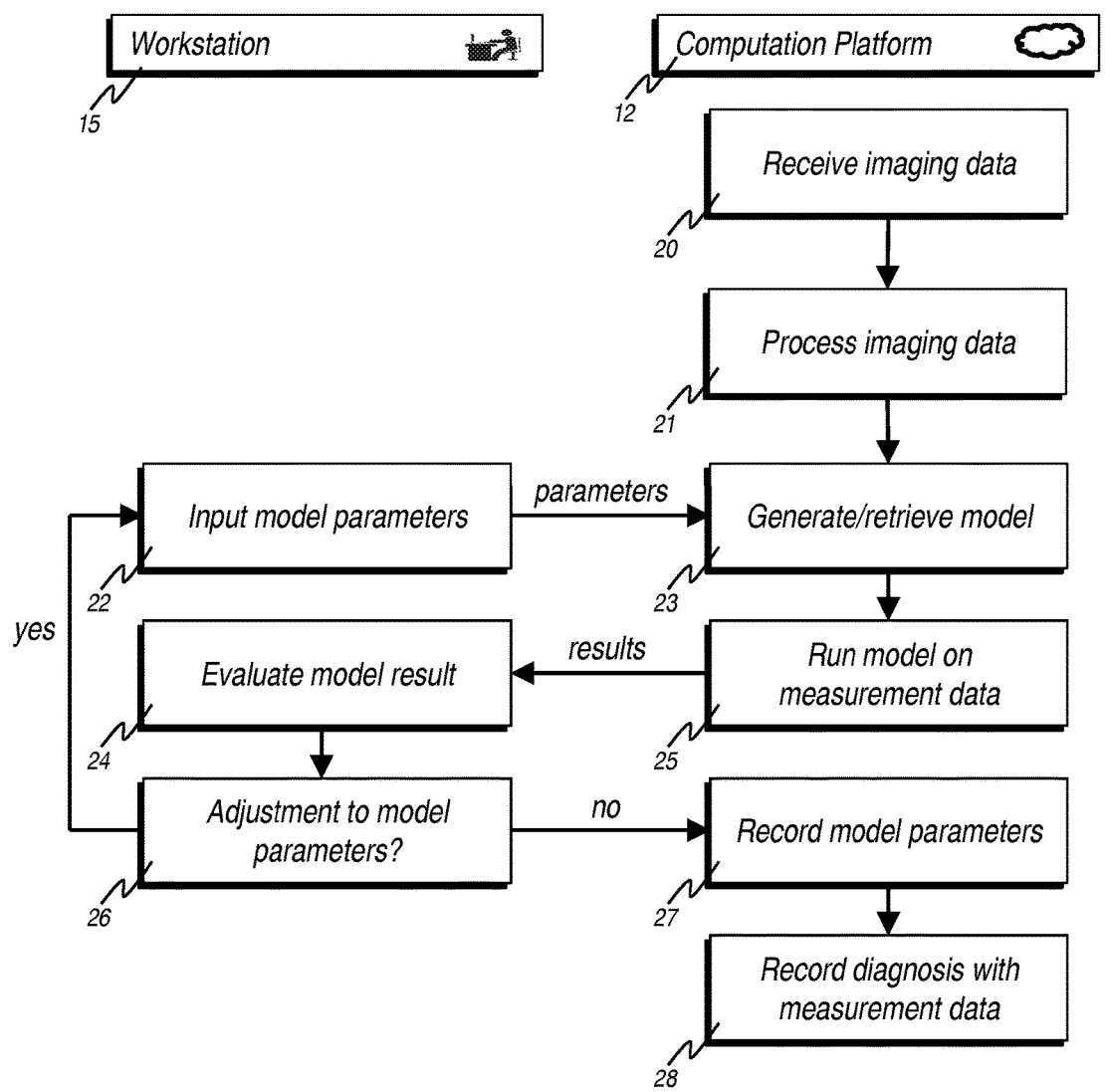
FIG. 2 schematically shows a flow chart according to embodiments of the disclosed subject matter.

FIG. 2 provides an overview of a workflow of using a model and the computation platform 12 from the work station 15. In step 20 the computation platform 12 receives imaging data from local storage 11 or directly from scanning device 10. The imaging data is processed in step 21 (more possible details of the processing step are described in reference to FIG. 3). The professional at the work station 15 sends model parameters to the computation platform 12 in step 22. These model parameters can form a "basal model" for use on the imaging data. The model parameters can comprise parameters for the model that will be used. For example the model parameters can specify which training data is to be used or which basic model is to be used.

With the term "basic model" is understood what the core model algorithm is, for example one of support vector machine, decision tree, decision forest, adaboost, boosted stumps, etc.

In step 23 the model, including a decision function, is generated (or retrieved, in case the model parameters correspond or refer to a previously generated and stored model) by the computation platform 12. After the model is generated or retrieved, in step 24, the model is run on the imaging data. The results of the model calculation are then sent to the workstation for evaluation. The results of the model calculation can comprise e.g. a segmentation, a determination of one or more regions of interest, a classification of one or more regions of interest, or a combination of these. In step 25 the professional at the workstation 15 evaluates the model results which are presented visually on the workstation. The professional may decide that adjustments to the model or to the model parameters are needed in step 26. If adjustments are needed, new input parameters are input by the professional and sent by the workstation to the computation platform 12. The computation platform 12 will then re-apply step 23 making only new calculations where necessary by the new parameters.

This process will continue until the professional is satisfied with the results from the model. The skilled person can then send his feedback on that model and on the model calculation results to the client platform 12. The computation platform 12 will then record the final model parameters used in the model calculation in step 27.

The computation platform 12 may also store classification or diagnostic feedback from the professional. For example the computation platform may store a positive or a negative diagnosis of a certain condition (step 28). The (processed) imaging data used in the calculation can then become training data with associated ground truth for future model training.

In a variant, the feedback from the professional is used to incrementally update one or more selected decision functions of the model.

Models

The examples disclosed in reference to FIGS. 3, 4, 5A and 5B focus on the use Support Vector Machines (SVMs) as the underlying basic model of the calculation. However, the disclosure is not limited to SVMs. Further on, brief explanations about the application of this disclosure to decision trees and boosted stumps will be provided. The skilled person will be able to apply the principles behind the examples in this disclosure to other types of models.

FIG. 3 schematically shows a flow chart for a model calculation according to embodiments of the disclosed subject matter. The steps 31-36 can be seen as an exemplary implementation of the steps 20, 21, 23, 25 in FIG. 2, using a Support Vector Machine (SVM) as the basic model. However, for other types of basic models, the steps 31-35 may apply as well, with only the final classification 36 being dependent on the type of basic model.

In step 31, imaging data is acquired, for example by reading it from a storage or by receiving it from a scanning device. The imaging data is segmented in step 32. In the segmenting step, areas may be identified that correspond to certain organs (e.g. lungs, heart, breast, etc). After the segmentation, regions of interest may be determined in step 33. This can be done manually (e.g. an operator indicates which regions are to be investigated further) or automatically, for example using template matching to identify candidate nodules in an image followed by variational calculus to determine the outlines of the candidate nodules. Data corresponding to the regions of interest may be stored as processed imaging data.

It is possible that some of the steps 31-33 are already performed before the imaging data is delivered to the computation platform 12, for example as post-processing in a scanning device. In that case, these steps can be omitted.

Once the regions of interest or, in specific cases, the candidate nodules are selected or detected, the item of interest (the nodule) is segmented in step 34. The item of interest (nodule) is separated from its surroundings.

Features of said regions or nodules are calculated in step 35. In typical modules, a range of features is calculated. Many features are available to the skilled person, for example symmetry features, circularity, spikulation, etc. Also high level features can be included, such as age, gender, and body mass. All feature values together form a feature vector. The calculated features may be stored as processed imaging data.

By storing the regions of interest (candidate nodule) imaging data and/or the calculated feature vector data as processed imaging data, it may not be necessary to store the entire imaging data that was acquired in step 31. This can be advantageous to save storage space or if storing such patient data is not allowed.

The product of any one or combination of the steps 31, 32, 33, 34, 35 can be stored for future reference. The advantage of storing data later in the chain 31-35 is that generally less storage space is required and there may be fewer data privacy concerns. A disadvantage is a loss of flexibility. For example, if the result of the candidate nodule selection (step 33) is stored, after which the original (step 31) and segmented (step 32) imaging data is discarded, then it is not possible to later to use an improved candidate nodule detection algorithm. For different applications, different choices may be made concerning which data is stored.

Finally, in step 36 each region of interest or candidate nodule is classified by the Support Vector Machine. Typical outcomes of such a classification are "malignant" or "not malignant" (a binary outcome). However, it is also possible to design SVMs to have more than 2 possible outcomes (for example, including a stage of the cancer in case of a malignant classification) or even a floating point value outcome. The classification step 36 will be explained in more detail in reference to FIGS. 5A and 5B.

FIG. 4 schematically shows a flow chart for specifying details of a model calculation according to embodiments of the disclosed subject matter. The steps 41-45 can be seen as selections that the workstation 15 user makes in step 22 of FIG. 2 and supplies to the computation platform 12 as model parameters.

An important aspect of Machine Learning algorithms such as Support Vector Machines is the selection of data points that is used for training the ML algorithm. In general, more data points improve the quality and reliability of the ML algorithm's outcome. At the same time, noisy or erroneously qualified data points may detract significantly from the quality and reliability. Therefore, it is important to only use quality data points from a known source.

In step 41, the data points are selected. Typically, the operator of the work station selects the data points by identifying which sources are to be used for data points. For example, the operator may indicate that his/her previous diagnoses is to be used to provide data points. The operator may indicate that only diagnoses for patients with certain conditions (e.g. age, gender) is to be used. Alternatively or additionally, the operator may indicate that data points from a certain (prestigious) doctor or medical centre are to be used. It is envisaged that individuals or institutions who specialize in certain diagnoses, will make their diagnoses available as usable data points in the computation platform 12. This allows operators in whose practice a certain diagnosis is not frequently made, to obtain sufficient data points from a known and trusted source.

In step 42, a selection is made of the features to be used in the classification. Not every feature calculated in step 35 needs to be used in the classification step 36. For most Machine Learning applications, there are a number of core features that are required. Selecting the features is an important part of defining or tuning a model. Again, it is envisaged that an operator may select a feature subset by referring to a subset as used or defined by a leading individual or medical institution.

The kernel selection in step 43 is a selection that is appropriate for SVMs. The operator may pick a specific kernel, select a default kernel, or refer to kernel as selected by a certain individual or institution. This also holds for the soft-margin/penalty parameter selection in step 44. This parameter determines how much "slack" a Support Vector Machine can use to allow for noisy data points or partially overlapping sets.

The user may determine a cross-validation strategy in step 45. In a cross-validation strategy, a subset of the data points can be reserved for checking the consistency of the model. This helps to improve the reliability. Again, the operator can make his or her own selection, request a default value, or refer to a choice made by somebody else.

Once all parameters are set, the model can be generated in step 46. If the basic model is a SVM, the generation step will calculate the hyperplane(s) separating data points from different categories (more details in FIGS. 5A and 5B). In general, the generation step 46 will involve using all available data points to train the algorithm to predict outcomes for new, unclassified, data points. With the generated model, the cross-validation strategy of step 45 can be performed.

The outcome of the cross-validation can be a reliability indication. The reliability indication can provide information on the expected percentage of false positives, sensitivity, etc, depending on the purpose of the model and the meaning of the labels used in the classification. If the reliability is considered too low, the model can be improved, for example by adding extra data points. An operator may for example first attempt to train a model using only his own data points in step 41. If it then turns out in step 47 that the reliability is insufficient, the operator may go back to step 41 and add data points from a trusted source to improve the statistical robustness of the model. This will be shown in more detail in reference to FIGS. 5A and 5B below.

Figure 5A:
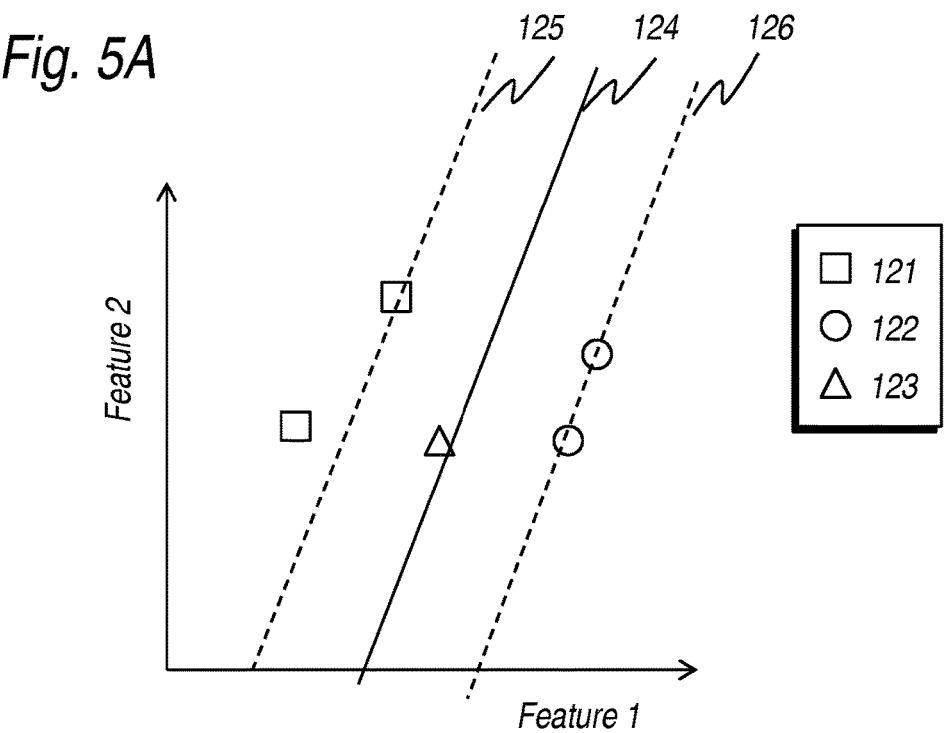
FIGS. 5A and 5B schematically illustrate the functioning of a Support Vector Machine model according to embodiments of the disclosed subject matter.
Figure 5B:
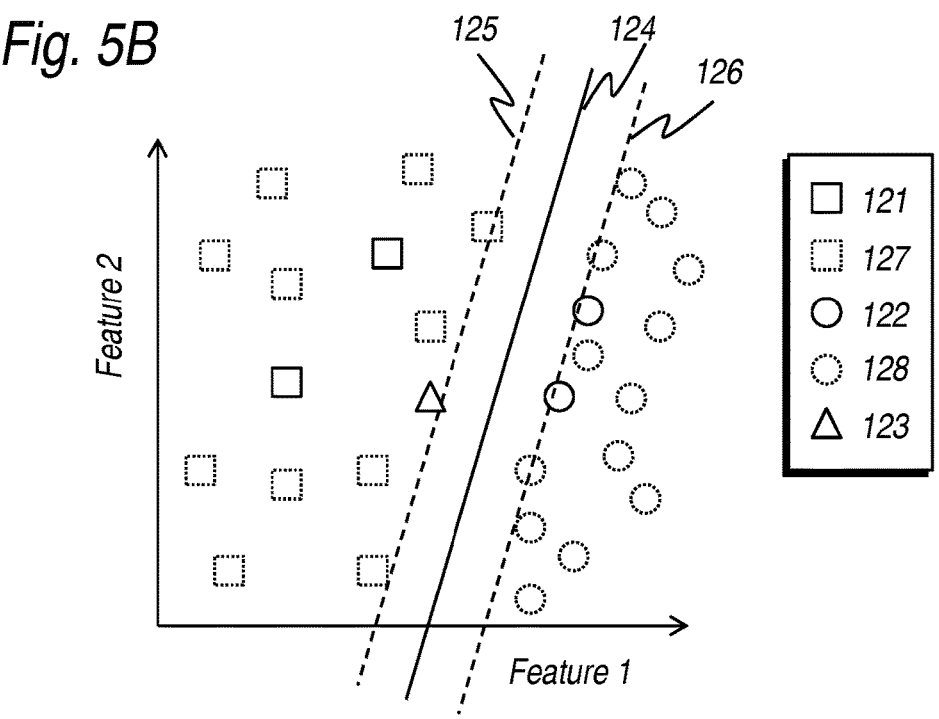

FIGS. 5A and 5B schematically illustrate the functioning of a Support Vector Machine model. For the sake of simplicity, an example SVM using only two features (feature 1 and feature 2) is used. In practice, the feature vector will usually have far more than two components.

In both figures, the squares 121, 127 indicate data points (in the two-dimensional feature space formed by feature 1 and feature 2 coordinates) with a certain label, e.g. +1. The circles 122, 128 indicate data points with another label, e.g. −1. Again for the sake of simplicity only two types of labels are used in the present example. One may for example indicate "malignant" and the other "benign". The skilled person will be aware that SVMs can be generalized for any number of labels or even for continuous values.

The triangle 123 indicates a data point that is to be classified (either +1 or −1 in the present example). For the present 2D example, an SVM takes the labelled data points 121, 127, 122, 128 into account and attempts to define a line 124 separating the points with different labels so that the gap, defined as the distance between lines 125 and 126 which run parallel to line 124 and which run through the squares and circles respectively nearest to line 124, is maximal. The line 124 determines the decision function of SVM. By determining the position of the triangle 123 relative to line 124, the label of triangle 123 can be predicted. The larger the distance of the triangle from line 124, the more confident the prediction of the label will be.

The situation in FIG. 5A is an exemplary result of an SVM calculation with relatively few data points (in this case 4, 2 for each label). The SVM can find a line 124 and corresponding gap which successfully classifies all 4 data points. However, it is easy to see that many different lines can be drawn to separate the 2 data points 121 from the 2 data points 122, and the line 124 may thus not be the correct one. In this situation, the triangle 123 is very close to the found line 124, and the classification of triangle 123 (in this example as a +1 data point, belonging in square group 121) is quite uncertain.

In FIG. 5B, the original set of data points 121, 122, 123 of FIG. 5A is maintained, but additional data points 127 (+1 group) and 128 (−1 group) have been added. This can correspond to the case wherein the operator in step 41 of FIG. 4, selects additional data points from a trusted source to improve the accuracy of the SVM. Now the line 124 calculated by the SVM to separate sets 121, 127 from 122, 128 is much more reliable. The triangle 123 is in this case classified as +1 (group 121, 127) with much more confidence.

If the data point 123 is classified by a professional and added to the data set, it is possible to update line 124, and thereby the decision function of the SVM, incrementally to account for the added data point. For SVMs, and indeed for many other ML algorithms, a full retraining using the data points 121, 127, 122, 128 is not needed. The addition of point 123, if it is close to the so-called decision boundary, will "nudge" lines 124, 125, 126 which make up the decision function and the gap by a small amount, which can be readily calculated and which strongly depends on the distance of point 123 to the line 124. If the point is far from the decision boundary, it will typically have a negligible effect on the decision function. Incrementally updating the decision function to accommodate a new data point has the advantage that the time-consuming retraining of the entire data set is not needed.

Figure 5C:
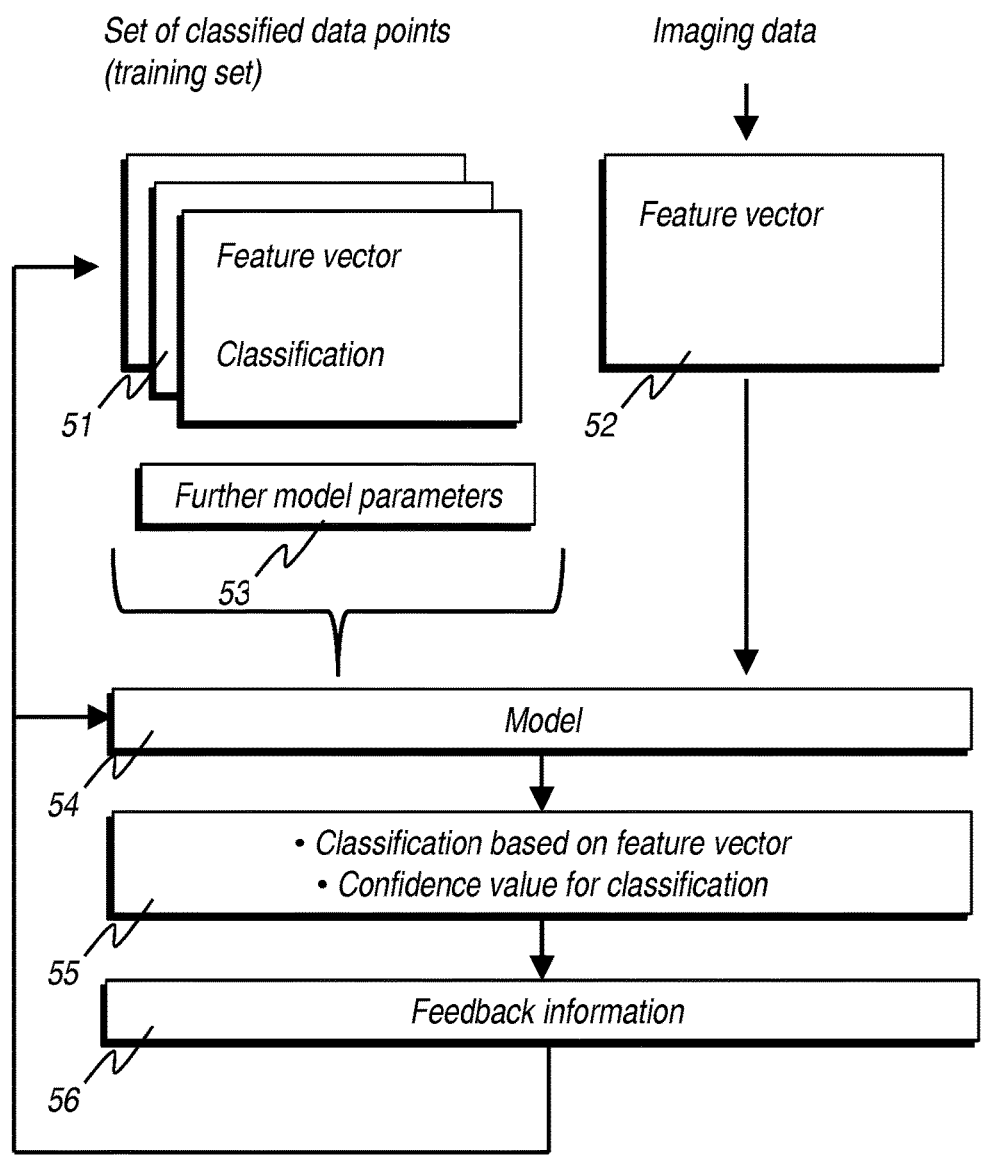
FIG. 5C schematically illustrates the functioning of a machine learning model according to embodiments of the disclosed subject matter.

FIG. 5C schematically summarizes the functioning of a SVM or a machine learning model in general. One or more sets of classified data points 51 are indicated as training data (e.g. one set is the set 121, 122 of FIG. 5A and another set is the set 127, 128 of FIG. 5B). The classified data point comprises at least the feature vector and the classification. The input 52 is the feature vector of the region of interest of the imaging data. This can be the point 123 of FIGS. 5A and 5B. The model 54 is further determined by the model parameters 53.

The model 54 has a decision function which projects feature vector 52 to a classification. The outcome 55 of the model 54 is the classification and, optionally, a confidence value for the classification. The confidence value can indicate how reliable the outcome is. Feedback information 56 based on the outcome can be added, together with the feature vector 52 which was used as input, as a new classified data point in data point set 51. This way, the model can be updated by incrementally updating the training set. Alternatively (or additionally), the feedback information 56 can be directly added to the model 54, to incrementally update the decision function to take the feature vector 52 feedback 56 into account. That way, a full retraining of the model using the updated training set 51 is not needed.

The above explanation in reference to SVMs can also be applied to other types of models. For example, decision trees can also be incrementally updated. First, it is checked if the decision tree already generates the correct classification for the newly added sample. If so, no further adjustment is needed. If it does not generate the correct classification, it is generally possible to determine the branch were a wrong decision is made and to update said branch. The same approach will work, mutatis mutandis, for boosted stump models. In general, it will be possible to incrementally update a model to introduce a new sample point in the training data, without actually retraining the model using the entire training data set.

Processing

Figure 6A:
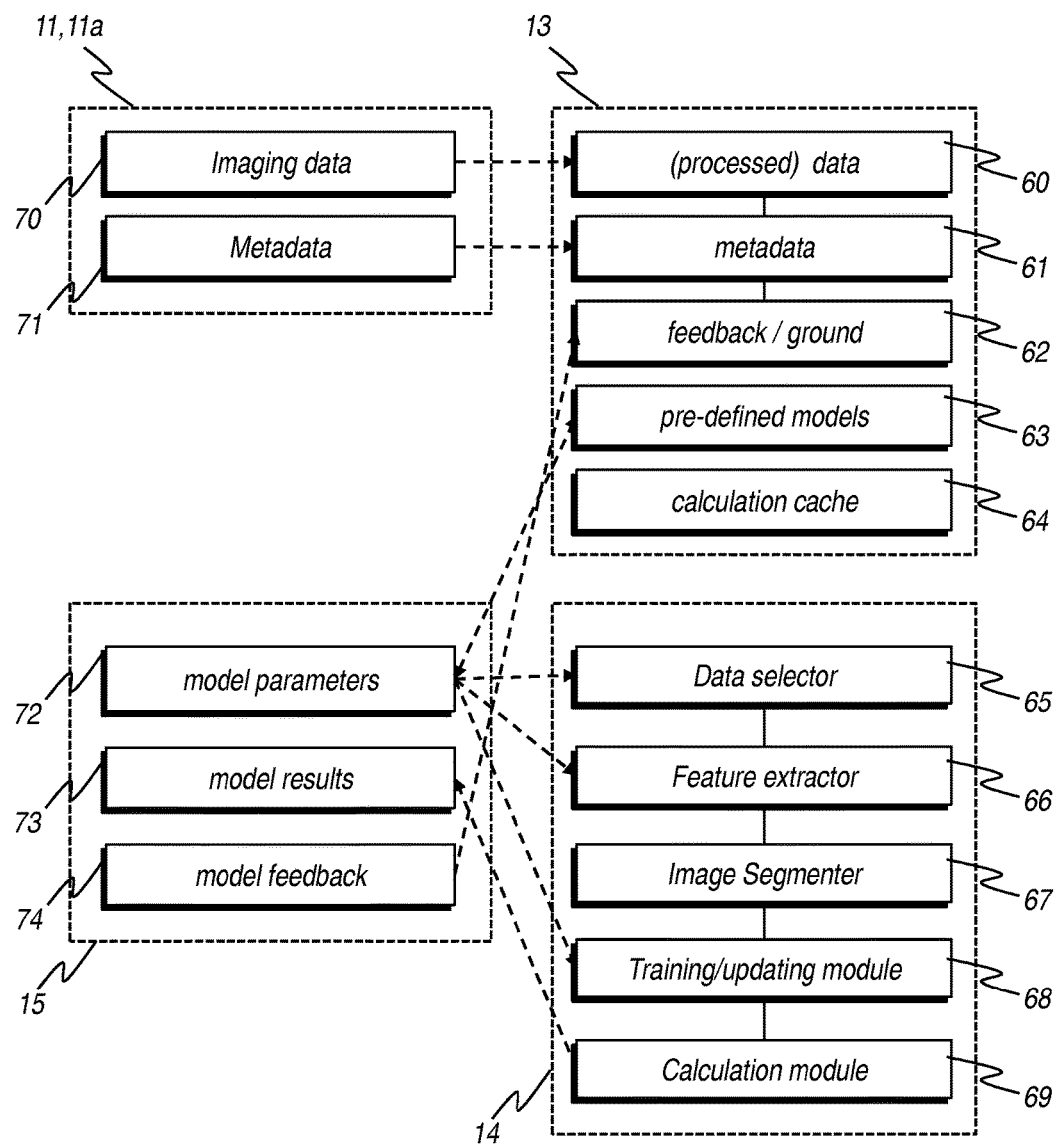
FIG. 6A schematically shows information flows between a workstation and a platform according to embodiments of the disclosed subject matter.

Returning now to the architecture as described in reference to FIGS. 1 and 2, FIG. 6A schematically shows information flows between a workstation 15 and a platform 12 according to embodiments of the disclosed subject matter.

The storage device 13 of computation platform 12 stores in number of different data types, of which some examples are given in FIG. 6. The storage device 13 can store pre-recorded (and usually pre-processed) imaging data 60, which has previously been received as imaging data 70 from an imaging data source, such as scanning device 10 or local storage 11. As was mentioned before, the product of any one or combination of the steps 31, 32, 33, 34, 35 of FIG. 3 can be stored for future reference as processed data 60. In addition, the storage 13 stores metadata 61 (associated with the processed data 60), which has been previously received from metadata source 11a or which has been manually entered. Also associated with the processed data 60 and the metadata 61, is feedback information or ground truth data 62. The feedback information can include information about the type of diagnostic information that is present in associated processed data 60. The metadata 61 associated with processed data 60 includes information about the patient and the patient's condition and about the type of scanner device 10 and the scanner modality used in obtaining the imaging data. The storage device 13 also include pre-defined models (e.g. sets of model parameters) 63. Furthermore, the storage 13 can store cache data 64 used by the modules of the computation means 14 of the platform.

The computation device 14 can include several modules, in part depending on the type of basic model that is used: a data selector 65, a feature extractor 66, an image segmenter 67, a training module 68, and a calculation module 69. These modules may be logical modules, implemented as one or more sets of computer executable instructions to be executed on a processing unit. The data selector 65 can retrieve processed data from the storage 13. The feature extractor 66 is configured to receive processed data from the data selector and/or the image segmenter and to calculate selected features in the received data. The calculated features may be stored in the calculation cache 64 for future reference. The image segmenter 67 can segment the image into distinct areas. The image segmenter 67 can make use of domain knowledge, so that for example a dedicated image segmenter module is provided for lung CT imaging data, and a different image segmenter for e.g. breast image data. The image segmenter 67 may also isolate objects in regions of interest, for example suspect nodules.

The training/updating module 68 can receive imaging data and feature vectors, and perform a machine learning training procedure to create a fully usable model. In addition, the training/updating module can take an existing (trained) model and incrementally update the model to add a new classified feature vector, e.g. based on feedback received in connection with a previous calculation on a feature vector.

Intermediate results of the training/updating may again be stored in the calculation cache 64 of storage device 13. After training or updating, the model can be stored in the pre-defined model storage 63. The training module 68 also includes validation programs to validate the training. For example, the training module can ascertain that sufficient data was available and that the machine learning algorithm resulted in a model which has a reasonable confidence value. In addition, the training module 68 can perform back testing and cross-correlation to validate models.

Finally, the calculation module 69 can take processed data as input, apply it in a model which has been trained by the training module 68, and calculate model results 72.

From the workstation 15, model parameters are set. Model parameters 72 may be defined by reference to a pre-defined model 63 stored in the storage device 13. For example, it is possible to refer to somebody else's stored model (which has been made available for use by others) or to refer to an ensemble of a number of pre-defined models. Such model parameters are also referred to as a "basal model" to indicate that the model parameters reference an existing, pre-defined model. In an ensemble calculation, the decision function of each model is provided with the same input and for each model a classification is calculated. Then the classifications are processed to generate an ensemble classification. The ensemble classification can be a weighted average of the classifications. It can also be a median or majority value of the classifications.

The model parameters 72 also can determine which data is to be used in training the model. Any combination of the selections in steps 41-45 of FIG. 4 can form model parameters 72. The model parameters 72 are used by the data selector 65 to determine which data points to use (see also data point selection step 41). The model parameters can indicate one or more specific sets of data points to be used.

For example, the model parameters may indicate that only imaging data from male patients of a certain age and with certain smoking habits are to be included in the training set. In this manner, the operator of the workstation 15 can create an ad-hoc model which is completely tailored to the circumstances of a specific patient or a specific research question. In another example, the operator chooses a set of data points from a certain colleague or institution to be used in the calculation. Being able to identify specific data point sets as model parameters has the advantages that the operator is no longer limited to his own set of data points (which may contain too few data points for a good training, as shown in FIG. 5A) while still offering complete and exact control over the model's input. The operator can make sure to only choose data points from trusted sources.

Likewise, the model parameters 72 can also specify which features are to be used by the model. In general, there are many feature points that can be calculated from imaging data. However, not all feature points are useful in all applications of machine learning. Therefore, a good selection of features to be used in the machine learning procedure is very important for a successful model. Again, the operator may refer to choices made by others, so that he or she can draw on the expertise of others who may have more experience.

Finally, the model parameters can specify how the training is to be performed or which cached training data is to be used in the calculation.

The calculation module 69 sends the model results 73 to the workstation 15 for inspection by the professional. If applicable, the professional will formulate model feedback information 74, which is subsequently stored in storage 13. Later, the thus stored feedback information 62 can be used in training new models.

Figure 6B:
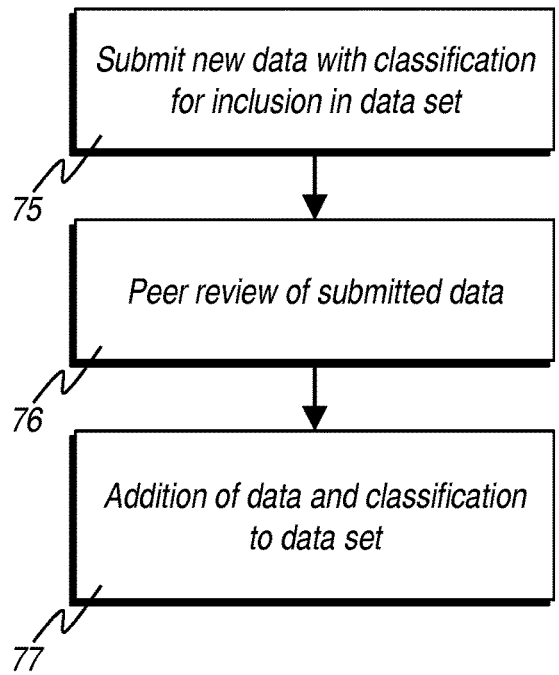
FIGS. 6B and 6C schematically illustrate a method for adding additional data according to embodiments of the disclosed subject matter.

FIG. 6B schematically shows a method of adding new data points to the computation platform. In step 75 the user submits the feature vector for the new imaging data, which was classified by the model, together with the final classification (feedback) to the computation platform for inclusion as a data point in a data set. The new data point can be added to an existing set of classified data points (for example a set that was indicated by the model parameters) or a newly formed set. In step 76, the submitted data point is reviewed by a peer user. This review may include a further check of the classification, to make sure that the set of classified data points is not polluted with erroneous data. If the review is positive, the data point is added to one or more sets of classified data points in step 77.

Figure 6C:
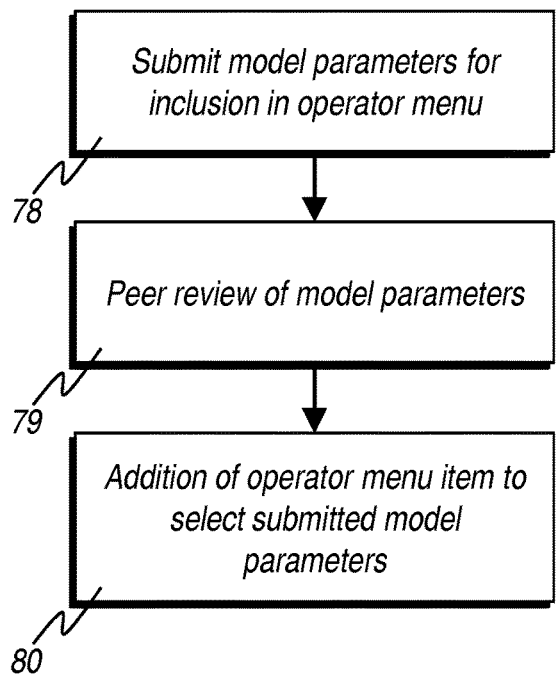
Figure 7A:
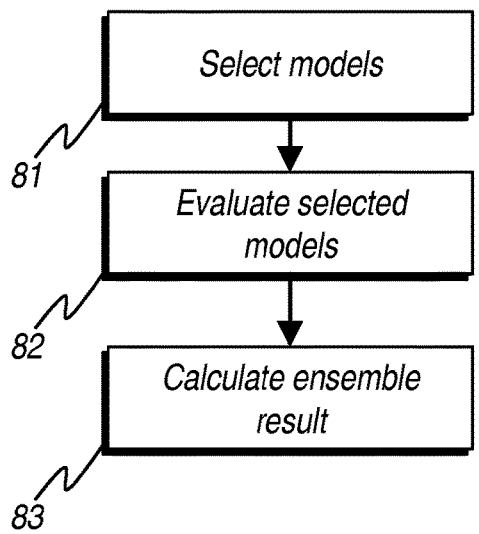
FIGS. 7A and 7B schematically illustrate a method for calculating an ensemble result according to embodiments of the disclosed subject matter.
Figure 8A:
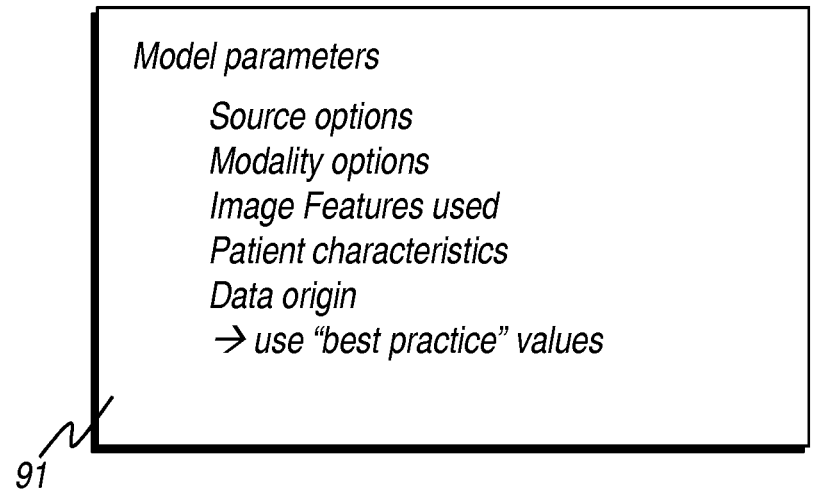
FIGS. 8A-8D show example screens for setting model parameters according to embodiments of the disclosed subject matter.
Figure 8B:
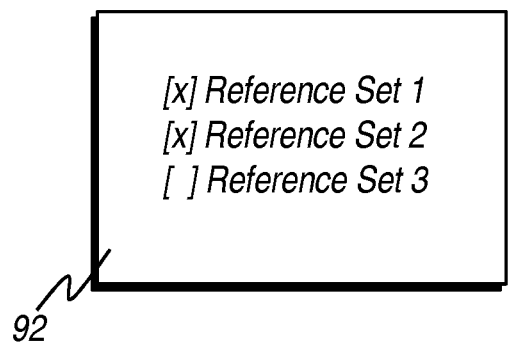
Figure 8C:
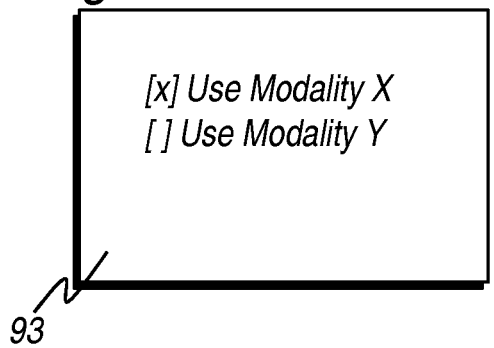
Figure 8D:
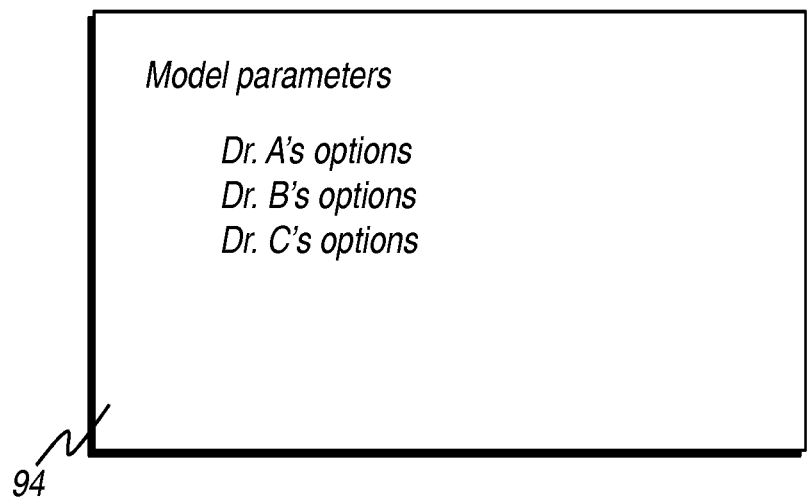
Figure 9:
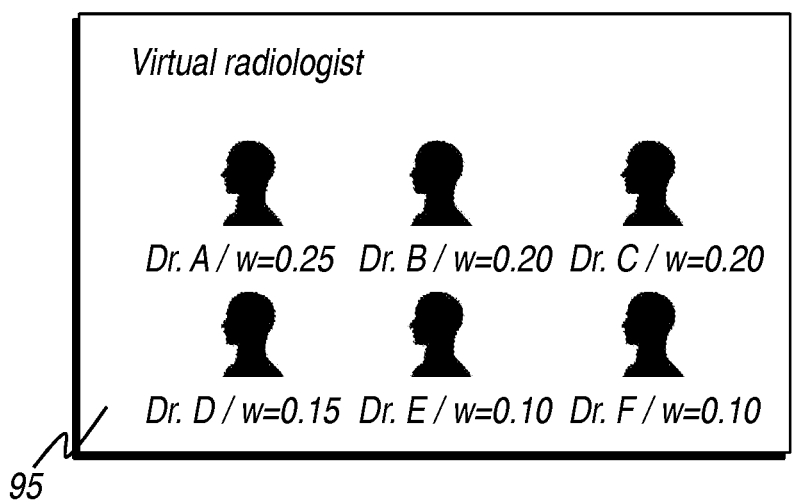
FIG. 9 shows an example screen of a virtual radiologist according to embodiments of the disclosed subject matter.

FIG. 6C schematically shows a similar method for submitting model parameters, for example for inclusion in an operator menu as shown in FIG. 7A, 8 or 9. In step 78, the model parameters are submitted. A peer review of the parameters takes place in step 79. If the review is positive, the model parameters are added as an operator menu item in step 80.

Figure 7B:
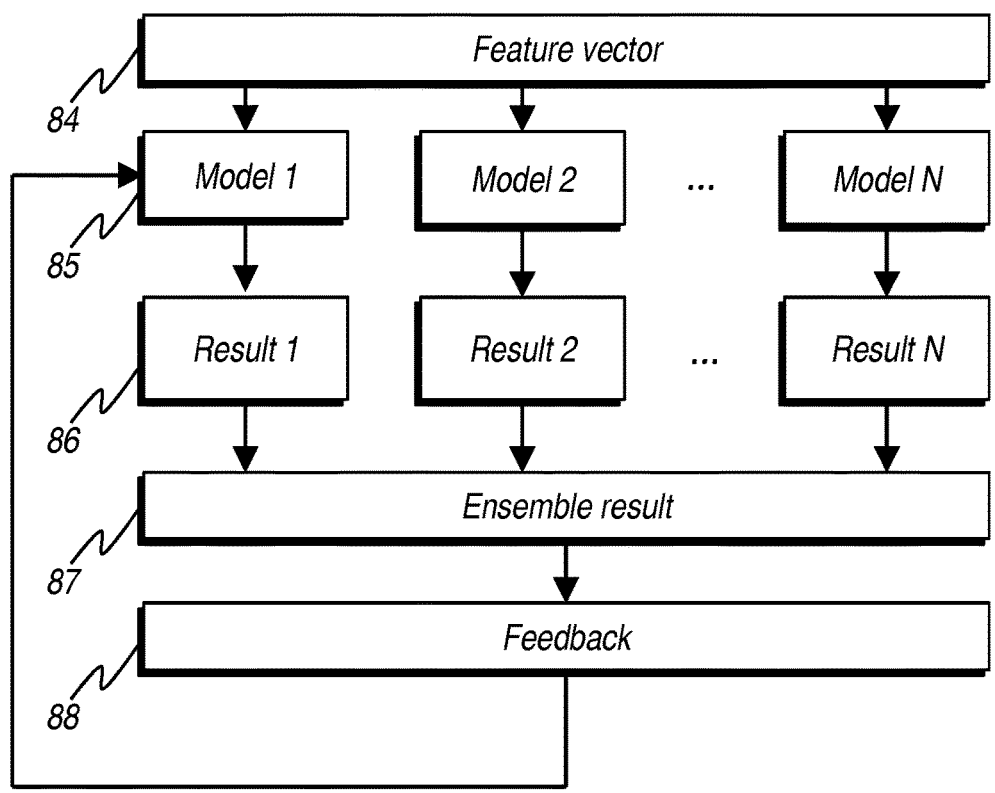

FIGS. 7A and 7B schematically illustrate a method for calculating an ensemble model result. In step 81, models 85 are selected, for example models 1, 2, . . . N. In step 82, these models 85 are provided with the same feature vector 84, and the N respective results 86 are calculated. In step 83, an ensemble result 87 is calculated based on the N results 86. There are various ways to calculate an ensemble result 87. A majority or median result can be taken. Alternatively, a weighted average can be calculated as the ensemble result. Feedback 88 concerning the ensemble result 87 can be sent to one or more of the models 85. In the present example, the feedback (which can be a final classification made by a professional based on the ensemble result) is fed back to model 1. As a result, the decision function of model 1 is incrementally updated to include feedback 88.

The computation platform storage 13 can thus store multiple models, and the calculation module 69 of computation device 14 can apply the same feature vector to a plurality of the models, after which the calculation module 69 calculates an ensemble result.

Workstation Interface

FIGS. 8A-8D show example screens for setting model parameters according to embodiments of the disclosed subject matter. FIG. 8A shows an example screen 91 of model parameters for the professional at the workstation 15 to specify. These parameters include source options, modality options, image features used, patient characteristics, and data origin. The workstation software will usually allow to use "best practice" values as defaults. The "best practice" values can be obtained from the computation platform which can maintain a database of model parameters and settings which show good performance in back-testing and cross-validation.

By specifying source options, the skilled person can indicate which scanning devices or which modalities are to be used in the training data for the model calculation. Modality options provides further selections for the used modality. By selecting image features, the professional can select which types of features are to be used by the model. There are generally many types of (visual) features that can be calculated from imaging data, but not all features are useful for every diagnostic application. It is an feature of the present disclosure that professionals can select which image features to use for the model calculation and moreover, these settings which become part of a basal model used can be shared among professionals so that a best of breed model can emerge through cooperation.

FIG. 8B shows a screen 92 for selecting which reference data sets are to be used for training and FIG. 8C shows a screen 93 for selecting which modality to use in case the input has multiple modalities. Any variation on the way imaging data is gathered can be a modality. For example, using a contrasting agent before a scan is a modality. Different equipment for imaging (even if the physical principle is the same) can be a modality too. By allowing a granular control over modalities, and thus distinguishing between the different imaging options, it becomes possible to correlate accuracy (for any given type of diagnostic) to the modality. For example, it may be that certain types of contrasting agent excel for certain types of detections, but hardly contribute to others. Likewise, equipment from different manufacturers may have different strengths and weaknesses.

FIG. 8D shows an example display 94 of a simplified screen for selecting a basal model. In display 94 the professional can select to use a basal model provided by Dr A, a model provided by Dr B, or a model provided by Dr C. In this manner the professional can quickly select model parameters that have been previously been used successfully. The user interface may present on request further information about the models, for example the type of sub-application and the results of back-testing and cross validation. The further information can also comprise references to professional literature which describe the model and results obtained with the model.

FIG. 9 schematically shows a display 95 for selecting an ensemble calculation. The professional can now define a model (here called "virtual radiologist") by combining various different models (here labelled "Dr.A", "Dr.B", etc). In a typical example, each of the models is provided and maintained by a professional; dr. A, dr. B, etc. In the present example of display 95 the ensemble result of the virtual radiologist is formed by a weighted average of the models of Drs A through F. By combining various models in an ensemble result, the results may be more reliable than any one of the single results. By keeping the various models separated from each other (until the ensemble result is calculated), it remains possible for the professional to perform a quality control. For example, if it turns out that Dr.B applies a methodology that the professional does not agree with, it is possible to remove the Dr.B's model (and underlying data) from the ensemble result.

Figure 10:
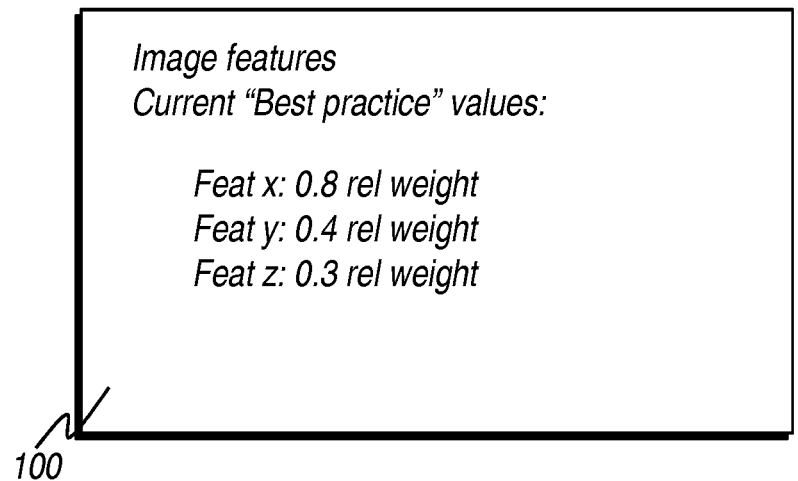
FIG. 10 shows an example screen for image features selection according to embodiments of the disclosed subject matter.

FIG. 10 schematically shows a display 100 for selecting image features for use in a model. The professional can make the computation platform 12 use default values by choosing the current "best practice" values. The professional can also specify exactly which imaging features to use and, if applicable, which weights these features should have in the model.

Figure 11:
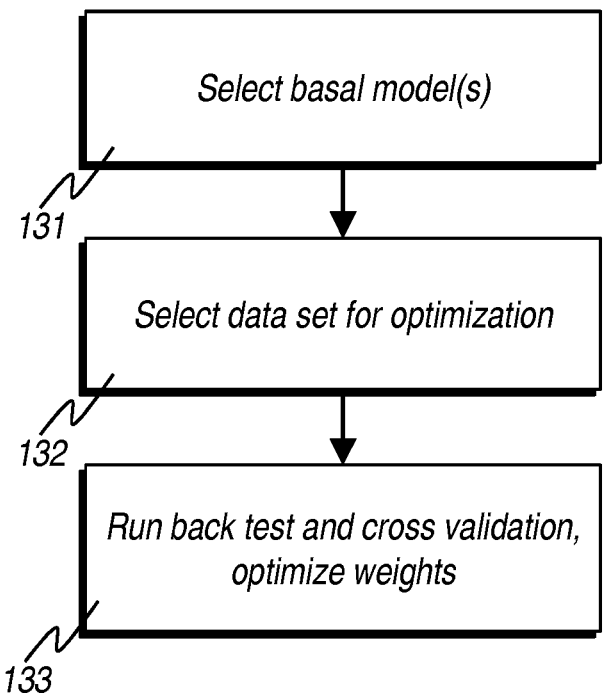
FIGS. 11 and 12 shows a flow diagram for a model calculation according to embodiments of the disclosed subject matter.

FIG. 11 shows a flow diagram for a model calculation according to embodiments of the disclosed subject matter. In step 131. The user selects a basal model or specifies model parameters. In step 132. The user selects which data is to be used for optimisation. For example, the user can select that data. According to certain patient characteristics such as for example age, habits, and/or gender is used for optimisation. The platform 12 (e.g. the training module 68) will then run a back test and cross validation using the selected basal model and the selected dataset for optimisation (step 133).

Figure 12:
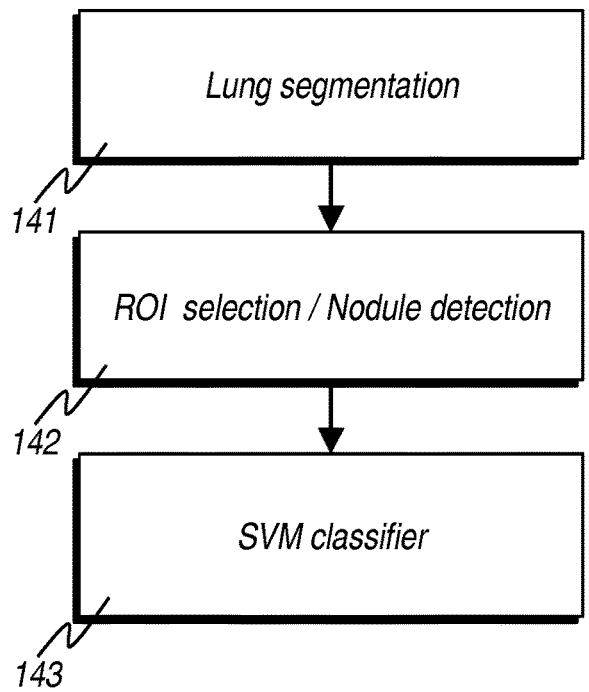

FIG. 12 shows a flow diagram for a model calculation, according to further embodiments of the disclosed subject matter. In step 141, imaging data representing a long is segmented. The results can be shown on a display of the work station, for inspection and verification. The imaging data can be 2-D or 3-D data. In step 142 nodules are detected to generate a list of so-called nodule candidates. Again, these candidates can be shown on the work station for inspection and verification. Finally, in step 143. A support vector machine (SVM) is used to decide whether the nodule candidates are malignant or not. The professional at the work station can inspect the classification and send feedback information to the computation platform.

Modalities

Figure 13:
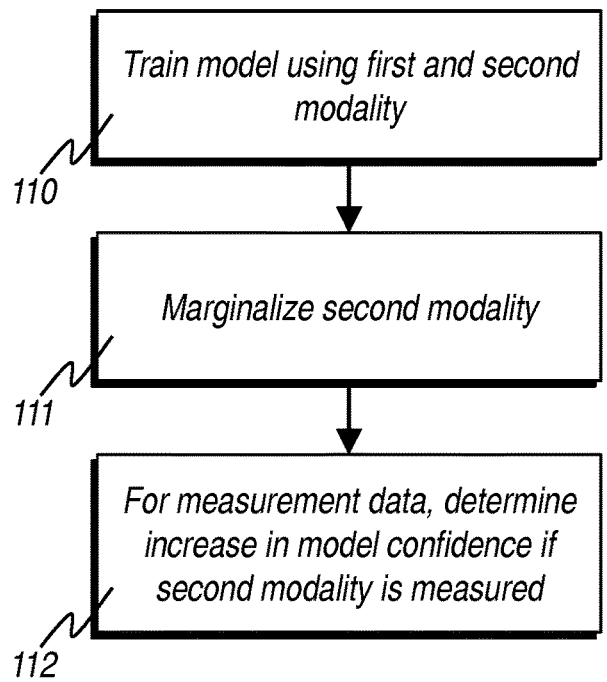
FIGS. 13 and 14 schematically show a flow diagram for estimating model confidence according to embodiments of the disclosed subject matter.

FIG. 13 schematically shows a flow diagram for determining an increase in model confidence if a second modality is measured. First, in step 110, the model is trained as described before using a first and second modality. The first modality can for example be an echo image and the second modality can be an MRI image. It will be recalled that a distinct type of scan (MRI, Echo, X-Ray CT, low-dose X-Ray CT, CT with contrast agent X) can be defined as a modality. In this context, also a biopsy procedure (for determining the nature of a nodule) can be considered a modality.

In step 111 the computation platform 12 makes calculations necessary to marginalise a second modality. Then for measurement data according the first modality, the model in the computation platform 12 will be able to estimate the increase in confidence if a second modality is measured. If there are multiple options for a second modality, the model will be able to estimate which modality of the multiple options will likely bring the most new information.

This advantageously makes it possible to use the model to determine whether or not a new test (e.g. a different type of scan or even a biopsy) will bring statistically relevant new information, in step 112. Since each new test brings discomfort for the patient as well as a financial burden, it is very useful to be able to determine whether or not such a new test would likely improve the quality/reliability of the diagnosis in a significant way.

Figure 14:
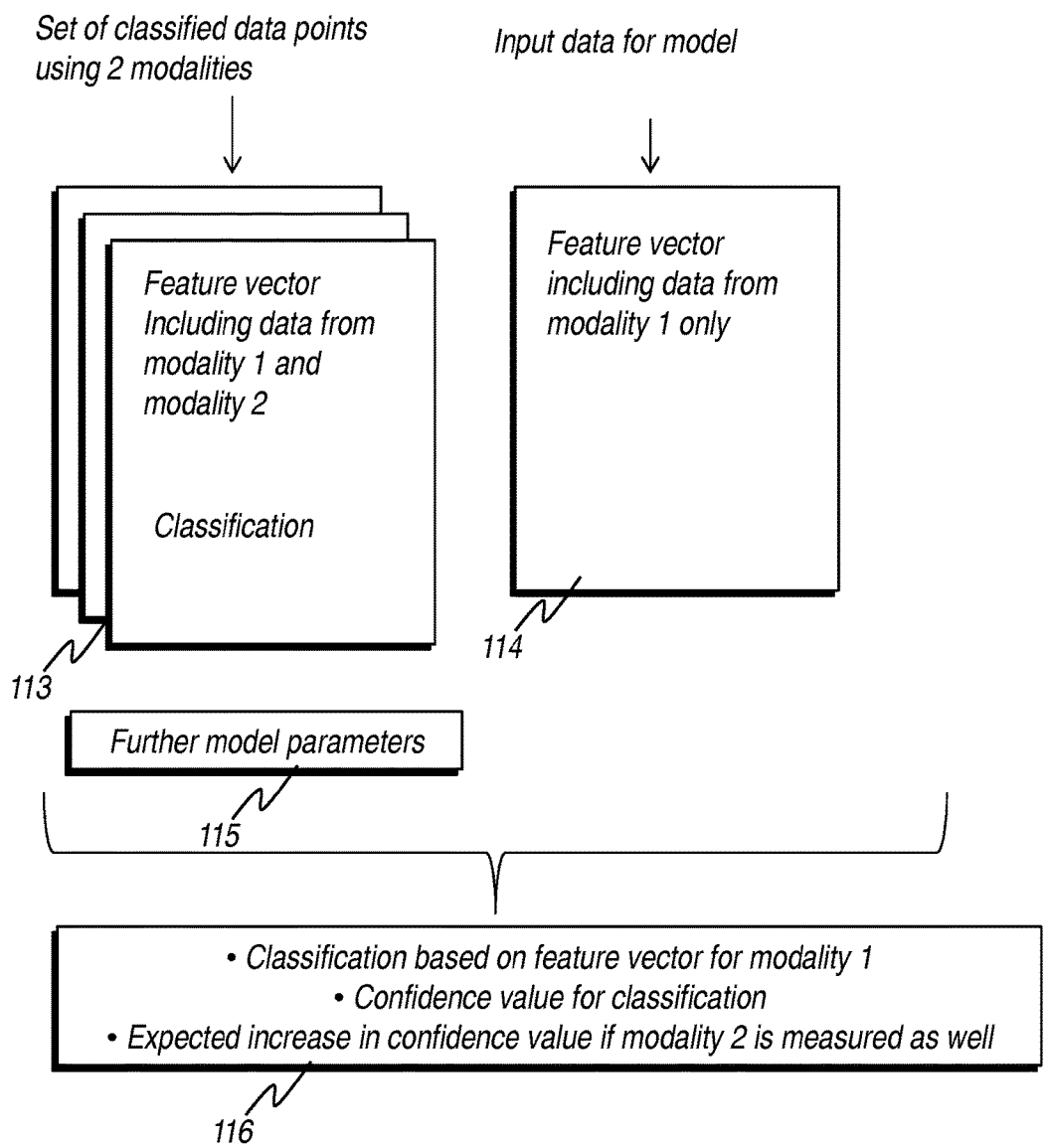

FIG. 14 schematically shows a method for determining whether or not a new test will bring statistically relevant new information. The classified feature vectors 113, used for the training of the model, include feature data from at least two two modalities (modalities 1 and 2). The input data feature vector 114 misses at least one of the at least two modalities. The features based on the second modality could be set to 0 in unclassified feature vector 114. Now the model output 116 can determine not only a classification (and corresponding confidence value) based on the feature vector of the input data and the data points used for training, but it can also determine an expected increase in confidence value if the at least one missing modality is added.

In case more than one modality is absent in the input data, the model can determine which modality would, in the present case, bring the most statistically relevant additional information. In other words, which modality would improve the diagnosis the most.

Figure 15A:
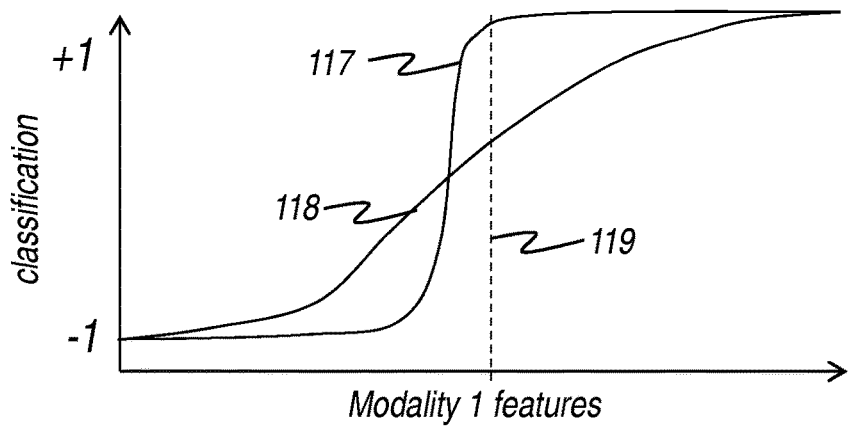
FIGS. 15A-15F schematically show various scenarios involving different modalities according to embodiments of the disclosed subject matter.

FIG. 15A schematically shows two scenarios using respective curves 117 and 118. The x-axis represents the modality 1 features (here represented as a one-dimensional feature, however this explanation holds also for the more general case with N modality 1 features). The curves 117, 118 represent, for two different models, the classification of the model based on the value of the modality 1 features. A classification value close to −1 or +1 is a high-confidence classification. A value in the middle between −1 and +1 is a low-confidence value.

Dashed line 119 represents an exemplary value of the modality 1 features of new imaging data which is to be classified. In the case of the first model (with curve 117) the classification will be +1 with a high degree of confidence. There is in that case little use in measuring a second modality—this will be unlikely to influence the obtained classification.

However, in the case of the second model (with curve 118), the classification will be quite uncertain. In this case, it may be useful to measure a second modality. The computation platform can calculate a likelihood that the additional modality will provide further information.

Figure 15B:
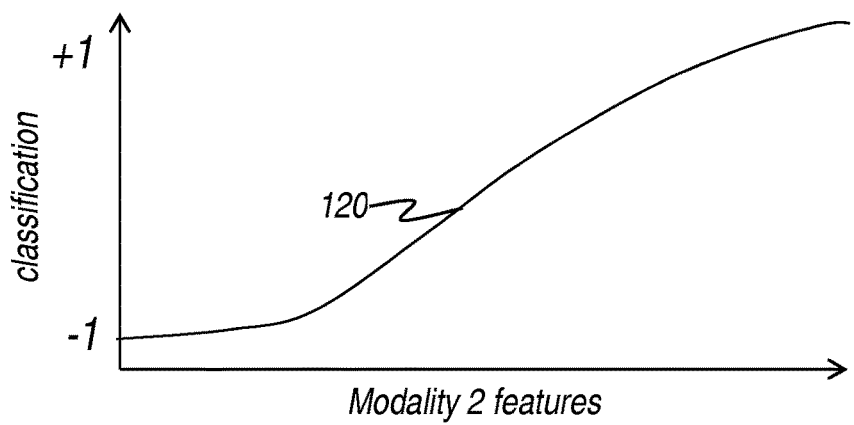
Figure 15C:
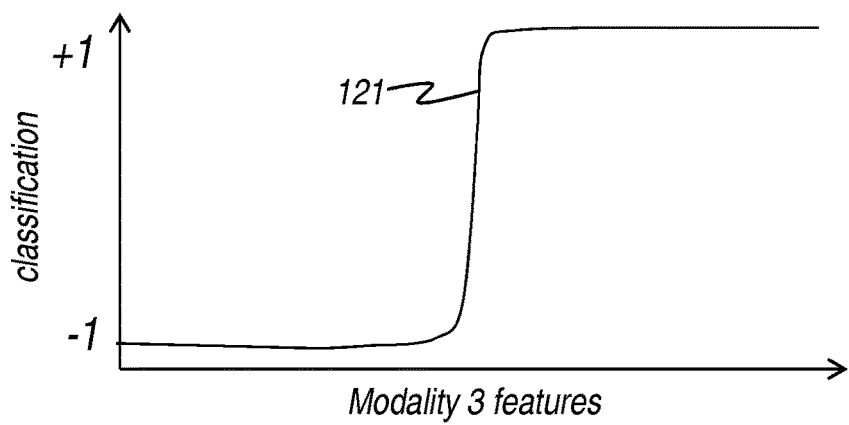

This process can be explained graphically using FIGS. 15B and 15C. FIG. 15B represents the curve for the classifications according modality 2 features (which are yet unmeasured) given that the modality 1 features value is established at the value denoted by dotted line 119 if FIG. 15A. FIG. 15C represents the curve according to modality 3 features (also not yet measured), with the same established value of modality 1 features. In this case, it is clear that only extreme values of the modality 2 features will give a clear −1 or +1 classification. In contrast, almost all values of the modality 3 features will give a clear classification. Therefore, modality 3 is most likely to give useful information given the currently known modality 1 features. Accordingly, the professional can propose to obtain the modality 3 information and forgo the modality 2 test.

Because the computation platform 12 has access to a large set of previous measurements involving various modalities, model calculations of the computation platform can marginalise the use of any second modality. In this way, the model can give an estimate of the increase in confidence if a second modality data were to become available.

It is also possible to take different outcomes (e.g. of various treatment options) in consideration. For example, if the data in the central platform is tagged with the later selected treatment and information related to the outcome thereof, it is possible to use the past experiences to improve choices in the future.

Figure 15D:
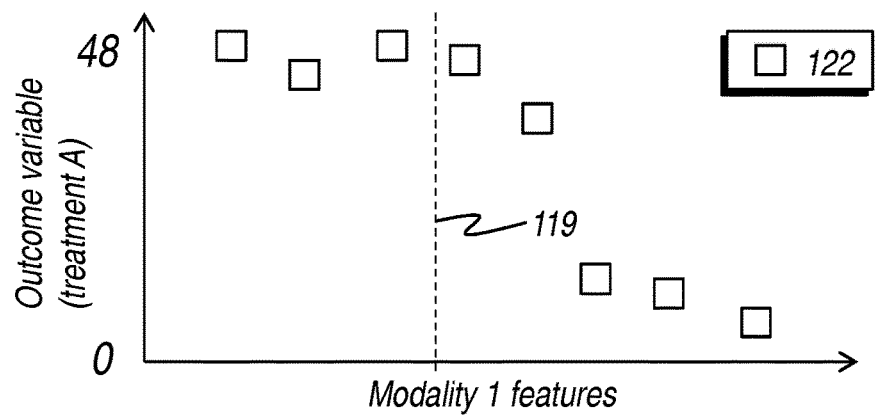

FIG. 15D illustrates schematically a number of outcomes for patients who, after a diagnosis involving a measurement of modality 1 features, received treatment A. Again, the modality 1 features are represented, for clarity only, as one-dimensional data along the horizontal axis. The vertical axis is in this case the outcome variable, which is the number of months of life after treatment A. Each outcome is represented as a square 122 at the intersection of the modality 1 feature value and the outcome. The same is shown in FIG. 15E, for treatment B with squares 123.

Figure 15E:
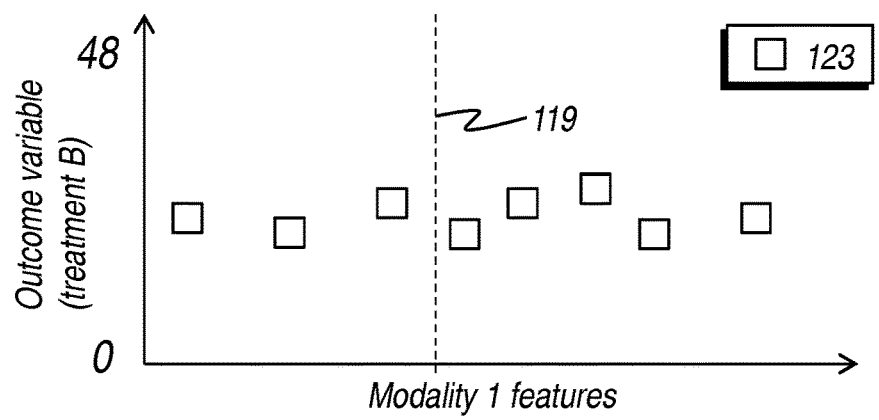

A clear pattern can be distinguished when comparing FIGS. 15D and 15E: while treatment B is about equally effective across all previously measured values of modality 1, treatment A shows a statistical dependency, where higher modality 1 values lead to lower outcome values. For both treatments, the average outcome is more or less equal (about 18 months). However, for a patient with modality 1 features according to line 119, treatment A has statistically a better outcome than treatment B.

Based on tagged patient data, the system is thus able, when there is a statistically significant relation between a modality and a treatment's outcome, indicate an advantageous course of treatment, even if the overall statistics of the treatments do not give a clear direction.

Figure 15F:
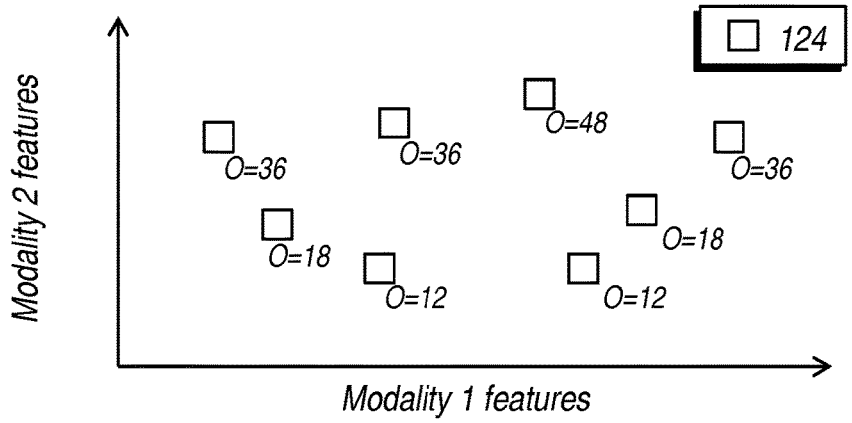

FIG. 15F shows a further scenario, wherein two modalities are considered. The outcome (again the number of months of life expectancy after a treatment) is now shown as a label for each point 124. Now assume that only modality 1 is measured. In the present case, there is no clear statistical relation between modality 1 features and the outcome, so that based on previous experiences, the outcome of the treatment could be anything between 12 and 48 months. However, when the potential modality 2 features are also considered, a statistical link emerges, where higher values of modality 2 features correlate with higher outcomes. In the present example, it might thus make sense to measure modality 2 in order to get a better estimate of a future treatment's outcome and thus make a better decision about treatment.

Patient Data

Figure 16:
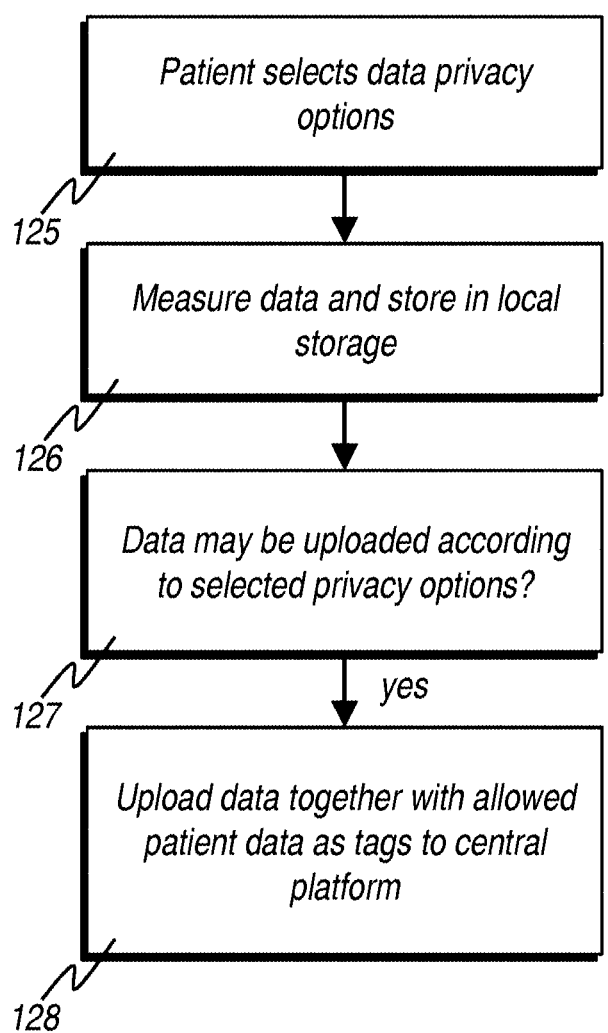
FIG. 16 shows a flow diagram for making patient data available according to embodiments of the disclosed subject matter.

FIG. 16 schematically shows a flow diagram for making patient data available to the computation platform 12. In step 125 a patient selects data privacy options for example through options on a paper form, or in an interactive computer application. In step 126 data is measured and stored in local storage 11, as described above. Patient metadata can be stored in a further local storage 11*a*.

In step 127, it is determined whether data may be uploaded depending on the selected privacy options. For example, the options may specify that only certain types of data are allowed for uploads. The options may also specify that the data must be made anonymous. The options may specify that certain aspects of the data are to be removed before uploading. Depending on the outcome of the check in step 127, in step 128 data is uploaded to the computation platform 12. By integrating the handling of patient privacy in the upload flow for the computation platform 12, it is possible to efficiently upload data from a wide variety of sources to the computation platform 12, while maintaining the option to exclude certain types of data if the patient's preferences or the regulations so require.

Concluding Remarks

In the foregoing description of the figures, aspects of the disclosure have been described with reference to specific embodiments. It will, however, be evident that various modifications and changes may be made thereto without departing from the scope of the disclosure as summarized in the attached claims.

In addition, many modifications may be made to adapt a particular situation or material to the teachings of the disclosure without departing from the essential scope thereof. Therefore, it is intended that the disclosure not be limited to the particular embodiments disclosed, but that the disclosure will include all embodiments falling within the scope of the appended claims.

It is also noted that when items are presented in a single drawn box in the figure, this is but a logical representation. In many real-world implementations, a plurality of such "boxes" can be implemented in a single chip or server, or functionality which is represented in a single box may be distributed (e.g. parallelized) over a number of different platforms. The skilled person is aware of such minor variations that are open to the implementer of this disclosure. The attached claims are not to be read as limited to specific segmentation of functionalities shown in the figures.

Combinations of specific features of various aspects of the disclosure may be made. An aspect of the disclosure may be further advantageously enhanced by adding a feature that was described in relation to another aspect of the disclosure.

It is to be understood that the disclosure is limited by the annexed claims and its technical equivalents only. In this document and in its claims, the verb "to comprise" and its conjugations are used in their non-limiting sense to mean that items following the word are included, without excluding items not specifically mentioned. In addition, reference to an element by the indefinite article "a" or "an" does not exclude the possibility that more than one of the element is present, unless the context clearly requires that there be one and only one of the elements. The indefinite article "a" or "an" thus usually means "at least one".

The invention claimed is:

1. Method for classifying a region of interest in medical imaging data, the method comprising:
   calculating a feature vector for at least one region of interest in the medical imaging data;
   projecting the feature vector for the at least one region of interest in the medical imaging data using a plurality of decision functions to generate a corresponding plurality of classifications;
   calculating an ensemble classification based on the plurality of classifications
   determining a diagnosis based on the ensemble classification,
the method further comprising
   receiving from the user feedback information concerning the ensemble classification;
   forming an additional classified feature vector from the feature vector and the feedback information; and
   updating at least one of the plurality of decision functions using the additional classified feature vector,
wherein each decision function is based on a different respective set of classified feature vectors.

2. The method according to claim 1, wherein the ensemble classification is a weighted average or ranked value of the plurality of classifications.

3. The method according to claim 1, wherein each decision function has been trained using the respective set of classified feature vectors to project a feature vector to a classification.

4. The method according to claim 3, wherein the at least one of the plurality of decision functions is updated by adjusting said decision function so that the updated decision function has effectively been trained using the respective set of classified feature vectors and the additional classified feature vector.

5. The method according to claim 4, wherein each decision function is based on one of a support vector machine (SVM), a decision tree, or a boosted stump.

6. The method according to claim 1, wherein the medical imaging data represents a human lung or a human breast.

7. The method according to claim 6, wherein the medical imaging data is a computer tomography (CT) image.

8. Computation platform comprising a computation device, the computation device comprising a processing unit, wherein the processing unit is adapted for:
   calculating a feature vector for at least one region of interest in received medical imaging data;
   projecting the feature vector for the at least one region of interest in the medical imaging data using a plurality of decision functions to generate a corresponding plurality of classifications;
   calculating an ensemble classification based on the plurality of classifications
   determining a diagnosis based on the ensemble classification,
wherein the computation device is further adapted for:
   receiving from the user feedback information concerning the ensemble classification;
   forming an additional classified feature vector from the feature vector and the feedback information; and
   updating at least one of the plurality of decision functions using the additional classified feature vector,
   wherein each decision function is based on a different respective set of classified feature vectors.

9. System of a computation platform according to claim 8 and a workstation, wherein the workstation is adapted to receive the ensemble classification and to transmit the feedback information.

10. Non-transitory computer readable medium comprising computer instructions for implementing the method according to claim 1.

* * * * *